(12) United States Patent
Qi

(10) Patent No.: US 9,170,144 B2
(45) Date of Patent: Oct. 27, 2015

(54) MULTIFUNCTIONAL FLUID LEVEL AND QUALITY SENSING DEVICE

(71) Applicant: Baohua Qi, Columbus, IN (US)

(72) Inventor: Baohua Qi, Columbus, IN (US)

( * ) Notice: Subject to any disclaimer, the term of this patent is extended or adjusted under 35 U.S.C. 154(b) by 278 days.

(21) Appl. No.: 13/938,230

(22) Filed: Jul. 10, 2013

(65) Prior Publication Data

US 2015/0013646 A1 Jan. 15, 2015

(51) Int. Cl.
| | |
|---|---|
| *G01F 23/26* | (2006.01) |
| *G01F 23/24* | (2006.01) |
| *G01N 27/12* | (2006.01) |
| *G01F 23/74* | (2006.01) |
| *G01N 33/00* | (2006.01) |
| *G01F 23/296* | (2006.01) |

(52) U.S. Cl.
CPC ............ *G01F 23/263* (2013.01); *G01F 23/246* (2013.01); *G01F 23/2962* (2013.01); *G01F 23/74* (2013.01); *G01N 27/123* (2013.01); *G01N 33/00* (2013.01)

(58) Field of Classification Search
CPC ...... G01F 23/263; G01F 23/74; G01N 27/123
USPC .......... 123/479, 198 D; 73/304 C, 295, 61.76
See application file for complete search history.

(56) References Cited

U.S. PATENT DOCUMENTS

| | | | | |
|---|---|---|---|---|
| 3,580,074 | A * | 5/1971 | Wescott et al. ............. | 73/304 C |
| 4,862,393 | A * | 8/1989 | Reid et al. .................... | 701/29.5 |
| 5,382,942 | A * | 1/1995 | Raffa et al. ................ | 340/457.4 |
| 5,607,002 | A * | 3/1997 | Siegele et al. ................. | 141/198 |
| 6,443,006 | B1 * | 9/2002 | Degrave ...................... | 73/304 C |
| 6,629,627 | B1 * | 10/2003 | Siegele et al. .............. | 222/464.1 |
| 8,078,414 | B2 * | 12/2011 | Matsunaga ..................... | 702/55 |
| 8,340,928 | B2 * | 12/2012 | Sun ................................ | 702/52 |
| 2010/0154534 | A1 * | 6/2010 | Hampton .................... | 73/304 C |
| 2010/0180663 | A1 * | 7/2010 | Sun ................................ | 73/1.02 |
| 2012/0186334 | A1 * | 7/2012 | Steinhauser et al. ......... | 73/61.76 |

* cited by examiner

*Primary Examiner* — Mahmoud Gimie

(57) ABSTRACT

A multifunctional fluid level and quality sensing device including a fluid level sensor and a capacitive sensor for detecting fluid level, fluid quality, errors in the sensing device, and issues in a fluid delivery system. In detecting fluid level, impedance of the capacitive sensor is used in improving sensing performance of the fluid level sensor, while in detecting fluid quality and errors in the sensing device, an expected impedance range with an upper boundary value and a lower boundary value is calculated, and a fault is generated when the measured impedance value is out of the expected impedance range. The fluid level and quality sensing device can also be used in a fluid delivery system for detecting system issues, and the results can be used for further isolating errors in the system. Operating status of higher level system provides more information for this purpose.

20 Claims, 10 Drawing Sheets

| Fault Flags And Values | | In-range High of Sensor 110 | In-range Low of Sensor 110 | Stuck-in-range of Sensor 110 | In-range High of Sensor 100 | In-range Low of Sensor 100 | Stuck-in-range of Sensor 100 | Fluid quality | Dosing System Issues | Vehicle Speed Sensor or Fluid tank issues |
|---|---|---|---|---|---|---|---|---|---|---|
| F1 | 1 | X | | X | | X | X | X | | |
| F2 | 0 | | | | | | | | | |
| F1 | 0 | | X | X | X | | X | X | | |
| F2 | 1 | | | | | | | | | |
| F3 | 1 | | | | X | | X | | X | |
| F4 | 0 | | | | | | | | | |
| F3 | 0 | | | | | X | X | | X | |
| F4 | 1 | | | | | | | | | |
| F5 | 1 | X | | X | | | | | X | |
| F6 | 0 | | | | | | | | | |
| F5 | 0 | | X | X | | | | | X | |
| F6 | 1 | | | | | | | | | |
| Fs | 1 | | | | X | | | | | X |
| Fk | 1 | | | | | | X | | | X |

FIG. 6

MULTIFUNCTIONAL FLUID LEVEL AND QUALITY SENSING DEVICE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF THE INVENTION

This present application claims priority from U.S. provisional application No. 61/671,830 having the same title as the present invention and filed on Jul. 16, 2012.

The present invention relates to a device for detecting fluid level and issues in a fluid delivery system, and more particularly, to a multifunctional device for detecting fluid level, sensor failures, fluid quality issues, and delivery faults in a fluid delivery system in which the multifunctional device is positioned.

BACKGROUND OF THE INVENTION

In some applications, e.g. in a fueling system of an engine, or a DEF (Diesel Exhaust Fluid) delivery system of a SCR (Selective Catalytic Reduction) apparatus, fluid level needs to be maintained above a certain level, and fluid quality issues, such as impure fluid or diluted fluid, need to be detected for avoiding deterioration in system performance and damages to the system. In these applications, normally a fluid level sensor and a fluid quality sensor are used for measuring fluid level and monitoring fluid quality.

Fluid level sensors can be either mechanical fluid level sensors or non-contact sensors. A commonly used mechanical fluid level sensor is a reed switch sensor which has magnetic reed switches activated by a force created with a magnetic float, while an ultrasound fluid level sensor is a non-contact sensor measuring fluid level using an elapsed time starting from the transmission of an ultrasonic sound wave to the reception of an echo.

A variety of sensors can be used in monitoring fluid properties. For example, a conductivity sensor can be used to measure the impedance or conductivity of a fluid, and a tuning fork sensor is able to detect changes in fluid density. However these sensors normally are point sensors, i.e., only fluid properties in a local area can be measured. As a result, it is difficult to detect a simple tampering to a fluid, e.g., disposing the sensor into a jar filled with a normal fluid and delivering a different fluid instead.

In the fluid level and fluid quality sensing, sometimes the rationality of the sensors needs also to be monitored to avoid false detections. Rationality errors of a sensor are in-range errors with which a sensing value obtained from the sensor is still within a normal sensing range, however, it is out of an error tolerance. Normally indirect methods are used in monitoring the rationality. For example, in a DEF delivery system of a SCR apparatus, a change in fluid level can be calculated using the amount of DEF being released if there is no refill or drain. Thereby, rationality of the fluid level sensor can be examined by comparing the calculated fluid level value to the sensing value. In the SCR apparatus, quality issues can be detected by using the deNOx efficiency of the apparatus, i.e., when a low deNOx efficiency is detected, a possible cause is diluted DEF. And these fluid quality issues can be further compared to the results obtained from the fluid quality sensor to verify its rationality. However, in the indirect methods, a few factors may significantly affect the diagnosis. For example, in the diagnostic methods mentioned above, slosh in DEF fluid and dosing accuracy may significantly affect the diagnosis of the fluid level sensor rationality, and the fluid quality sensor rationality is subject to the effects of DEF dosing accuracy, NOx sensor accuracy, and control algorithms used in the SCR apparatus. These effects may cause a false passing or a false alarm.

For overcoming the problems associated with the fluid quality sensing and sensor rationality diagnosis, it is then an objective of the present invention to provide a multifunctional sensing device that is able to detect both of quality level and fluid quality in a bulk fluid. The detection of fluid quality in the bulk fluid makes it difficult to tamper the fluid. A further objective of the present invention is to provide a sensing device that not only can detect fluid level and fluid quality, but is also able to detect rationality issues in the sensing device itself. Yet another objective of the present invention is to provide a fluid level and quality sensing device that is able to detect failures in a fluid delivery system in which the fluid level and quality sensing device is positioned. Yet another objective of the present invention is to provide a diagnostic method that is able to isolate issues in fluid quality, sensors, and the fluid delivery system.

BRIEF SUMMARY OF THE INVENTION

In accordance with the present invention, a multifunctional sensing device with a fluid level sensor and a capacitive sensor is provided for detecting fluid level, fluid quality, and sensor rationalities.

In a preferred embodiment of the present invention, a fluid level and quality sensing device includes a controller, and a fluid level sensor and a capacitive sensor positioned in parallel in a fluid. Sensing values are obtained from the fluid level sensor by the controller and impedance of the capacitive sensor is measured. The fluid level sensing values are then used to calculate an expected impedance range of the capacitive sensor, and the measured impedance value is compared to the expected impedance range for examining fluid quality and sensor rationalities. In the fluid level and quality sensing device, the fluid level sensor can be either a mechanical sensor, such as a reed switch sensor, or a non-contact sensor, e.g. an ultrasonic sensor. And a temperature sensor can be positioned in the fluid for providing fluid temperature in compensating the calculation of the expected impedance range.

The capacitive sensor in the sensing device serves two purposes: one is fluid level sensing and the other one is fluid quality sensing. The sensitivity of the capacitive sensor to fluid quality creates uncertainty in sensing fluid level if the capacitive sensor is used alone. However, with the help of the fluid level sensor, fluid quality information can be obtained from the sensor impedance with only uncertainties caused by fluid level sensing accuracy and temperature, and when fluid temperature is used in obtaining the fluid quality information, the uncertainties can be further decreased. Reversing the calculation of the fluid quality information, with the uncertainties and a required fluid quality range, e.g. fluid type and concentration range, an expected impedance range of the capacitive sensor can be calculated. If the measured impedance is out of the expected range, then a failure is detected. This failure is either caused by a fluid quality issue or sensor rationality issues.

In the fluid level and quality sensing device, in addition to fluid quality sensing being improved with the help of the sensing values obtained from the fluid level sensor, the impedance of the capacitive sensor can also help improving fluid level sensing performance. Impedance of the capacitive sensor can be measured quickly and continuously. Accordingly, the change of impedance can be used for detecting fluid slosh and compensating sensing values obtained from the fluid level sensor. In an exemplary embodiment of the fluid level and quality sensing device, a reed switch fluid level sensor is used. The change in the measured impedance is used in providing fluid level sensing values in between two step sensing values obtained from the reed switch sensor. In another exemplary embodiment, the fluid level and quality sensing device includes an ultrasonic fluid level sensor. The impedance change is used for generating sensing values when the ultrasonic fluid level sensor is not able to provide a valid sensing value.

When a fluid level and quality sensing device is positioned in a fluid delivery system, the sensing device is also able to detect failures in the fluid delivery system. An exemplary embodiment of the fluid delivery system is a DEF delivery system of a SCR apparatus. In this fluid delivery system, the change in the impedance of the capacitive sensor is used to detect a slosh of the DEF, and the difference between two DEF volume values calculated using level sensing values obtained when there is no DEF slosh is compared with the amount of the DEF released by the DEF delivery system. If no refill or drain is detected, then the comparison result reveals issues in the DEF delivery system.

Fault flags generated in detecting issues in the fluid delivery system, sensors, and fluid quality can be used for isolating errors, and the operating status of higher level system provides more information for this purpose. In an exemplary embodiment of the present invention, a SCR apparatus is positioned downstream from an engine, receiving exhaust air from the engine. In this system, the relation between an energy ratio, which is the ratio of a change in exhaust air enthalpy to the energy released in burning fuel, and a DEF consumption ratio, which is calculated by dividing the amount of dosed DEF by that of injected fuel, provides an indication of issues in the system including both of the engine and the SCR apparatus. This information can be used for further isolating errors in the engine, the SCR apparatus, and system integrity.

BRIEF DESCRIPTION OF THE DRAWINGS

FIG. 6 shows a matrix of fault flags and issues in sensors and a DEF dosing apparatus.

DETAILED DESCRIPTION OF THE INVENTION

Figure 1A:
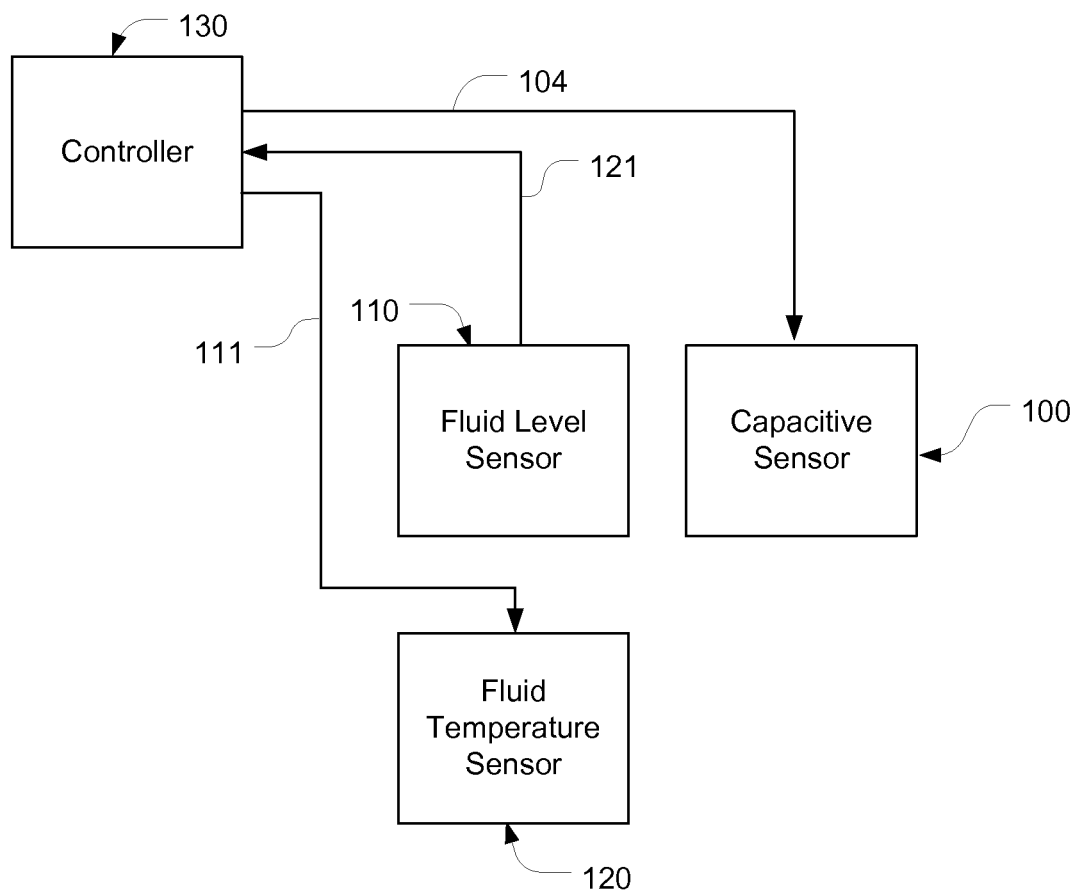
FIG. 1a is a block diagram of a fluid level and quality sensing device.

Referring to FIG. 1a, a fluid level and quality sensing device includes a fluid level sensor 110, a capacitive sensor 100, and a controller 130. The fluid level sensor 110 is in communication with the controller 130 through signal lines 121, while the capacitive sensor 100 links to the controller via signal lines 104. A fluid temperature sensor 120 can be further included in the sensing device reporting sensing values to the controller 130 through signal lines 111.

Figure 1B:
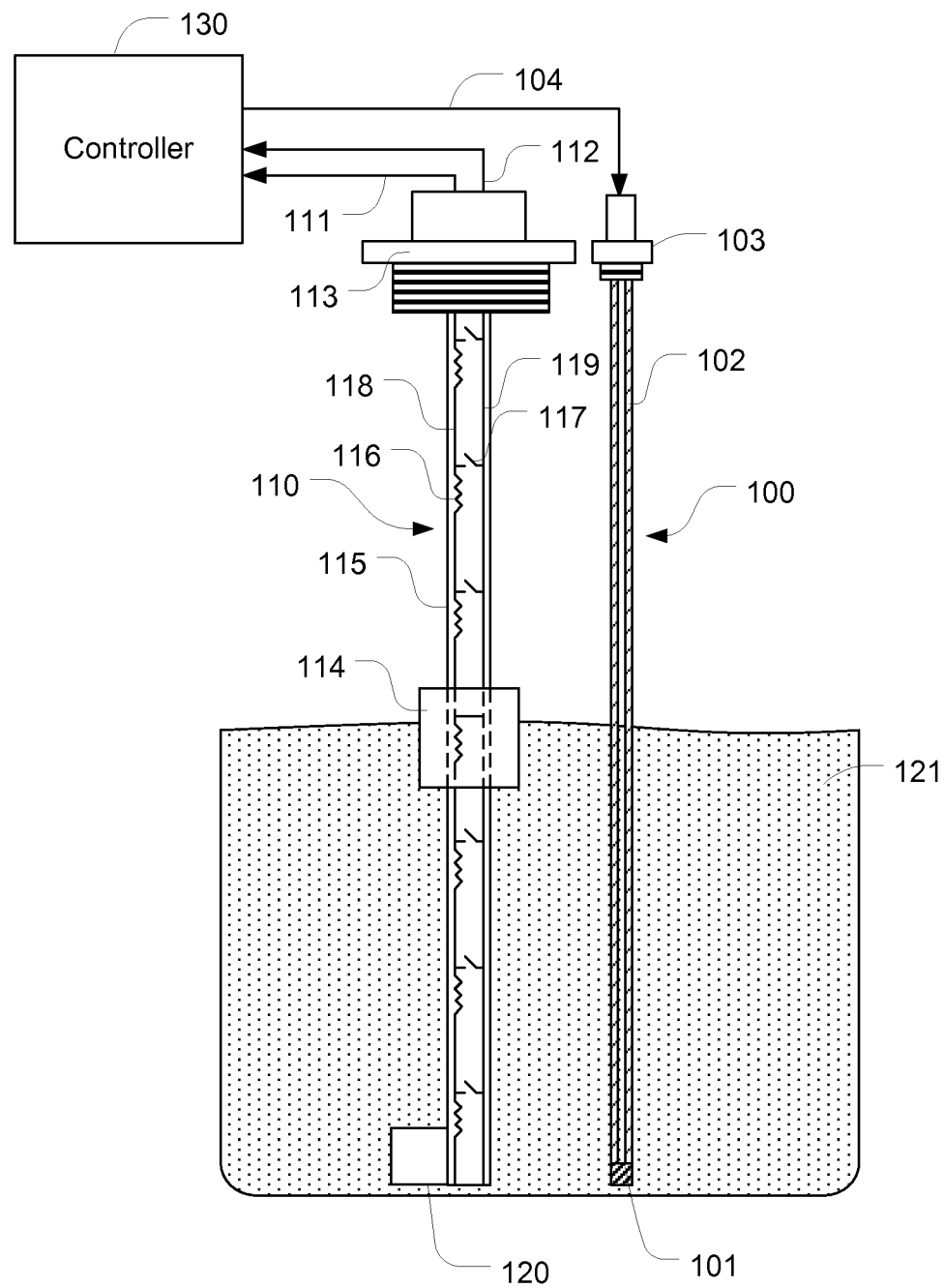
FIG. 1b is a diagrammatic illustration of a fluid level and quality sensing device with a reed switch level sensor and a capacitive sensor.

The fluid level sensor 120 in the sensing device can be a mechanical level sensor having a float changing position with fluid level. An embodiment of such a device is depicted in FIG. 1b. In this device, the fluid level sensor is a reed switch level sensor. The reed switch level sensor has a stem 115 with a resistor line enclosed inside. In the resistor line, resistors 116 are linked in serial by wires 118, and a wire 119 which connects to the resistors 116 through magnetic switches 117. Encircling the stem 115, a ring float 114 moves up and down along the enclosure. The ring float 114 has permanent magnets inside. Thereby when the ring float moves adjacent to one of the magnetic switches 117, under the magnetic force, the switch is tuned on, shorting the resistors 116 under the magnetic switch. By measuring the resistance change caused by the on and off of the switches 117, fluid level can be detected. On the top of the enclosure 115, there is a cap 113 and the resistance between one terminal of the resistor line and the wire 119 is measured by a controller 130 through the signal lines 112.

The capacitive sensor 100 includes electrodes 102 mounted in parallel in between a cap 103 and a nonconductive retainer 101. A stimulus signal is applied to the capacitive sensor 100 through signal lines 104 by the controller 130, and the capacitance is measured in the controller. The reed switch sensor 120 and the capacitive sensor 100 are immersed in a fluid 121, and the temperature sensor 120 is positioned at the bottom of the fluid.

Figure 1C:
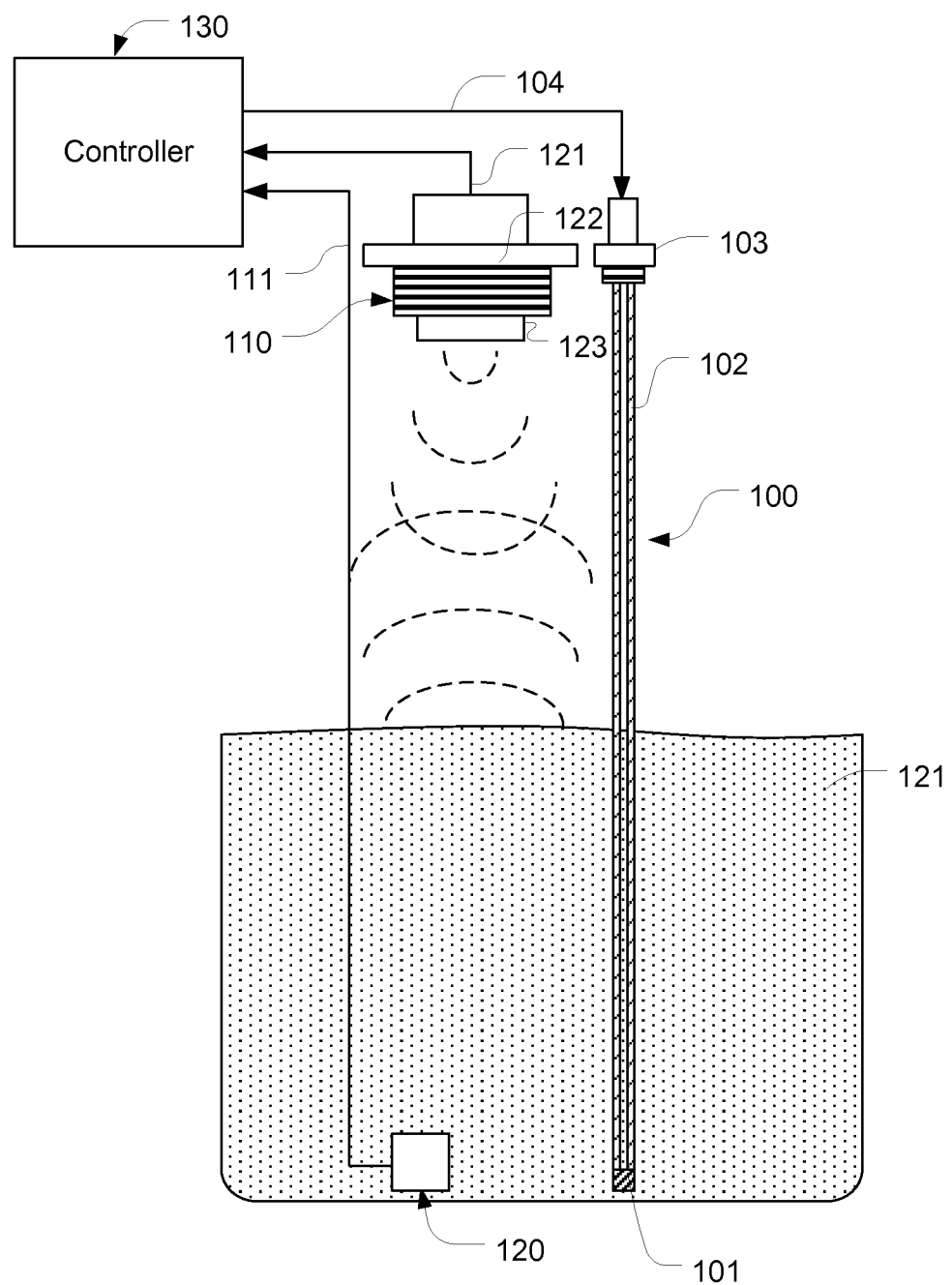
FIG. 1c is a diagrammatic illustration of a fluid level and quality sensing device with an ultrasonic level sensor and a capacitive sensor.

The fluid level sensor 110 in the sensing device can also be a contactless sensor, such as an ultrasonic sensor, or an optical sensor. A fluid level and quality sensing device with an ultrasonic level sensor is illustrated in FIG. 1c. In the sensing device, the ultrasonic level sensor 110 includes a transducer 123 and a cap 122. The ultrasonic transducer transmits an ultrasonic pulse perpendicular to the surface of the fluid 121, and receives echo signals. The fluid level position is then calculated by using the time delay between the transmitting and receiving of the ultrasonic signals, and the sensing values are sent to the controller 130 through the signal lines 121.

Figure 2:
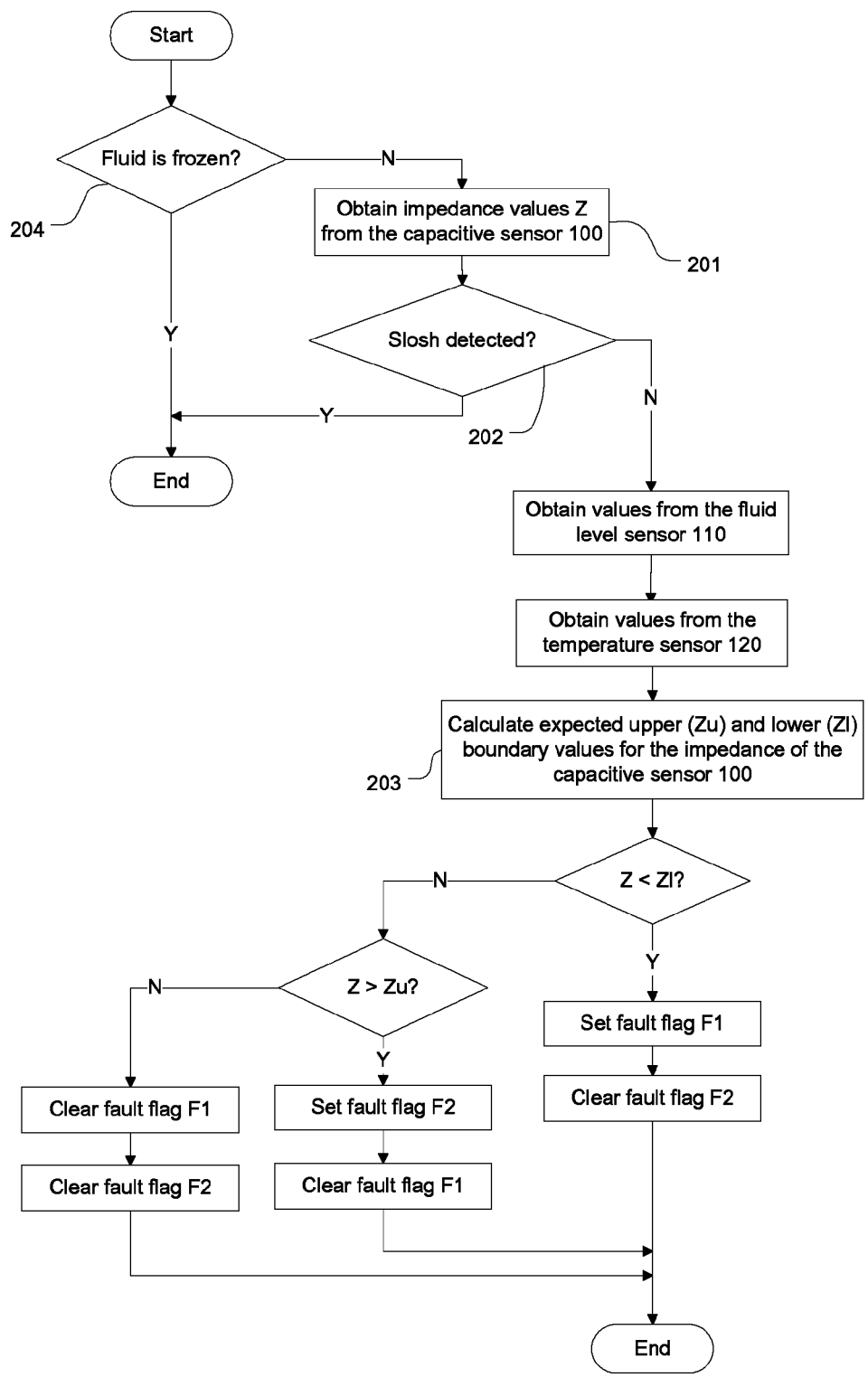
FIG. 2 is a flowchart of an exemplary service routine for a timer based interrupt running periodically for detecting fluid level and quality failures.

Sensing values obtained from the fluid level sensor 110 and the capacitive sensor 100 can be used for diagnosing failures in the sensors and the fluid. And the diagnosis can be realized with a service routine periodically running in the controller 130 for a timer based interrupt. As shown in FIG. 2, in an example of such a routine, at the beginning, the fluid status is checked in a step 204. If the fluid is frozen then the routine ends, otherwise, the impedance of the capacitive sensor 100, Z, is measured. The fluid status is checked thereafter. If the fluid is in slosh, then the routine ends, otherwise, sensing values are obtained from the fluid level sensor 110 and the temperature sensor 120, and expected upper and lower boundary values for the impedance of the capacitive sensor 100, Zu and Zl, are calculated. If the measured value Z is lower than the lower boundary value Zl, then a fault flag F1 is set and a fault flag F2 is cleared before the routine ends, otherwise, if the measured value Z is higher than the upper boundary value Zu, then the routine ends after the fault flag F2 is set and the fault flag F1 is cleared. Both of the fault flags F1 and F2 are cleared if the measured value Z is in between the upper and lower boundaries.

In the routine, the step 204 is to avoid measuring level value for a frozen fluid. The fluid status can be determined either with the sensing value obtained from the temperature sensor 120, e.g., when the temperature sensing value is lower than the freezing point of the fluid, then the fluid status is set to "frozen", or using the status of a fluid heater, which is energized when the fluid is frozen, e.g., the fluid status is "frozen" when the fluid heater is energized.

Figure 3:
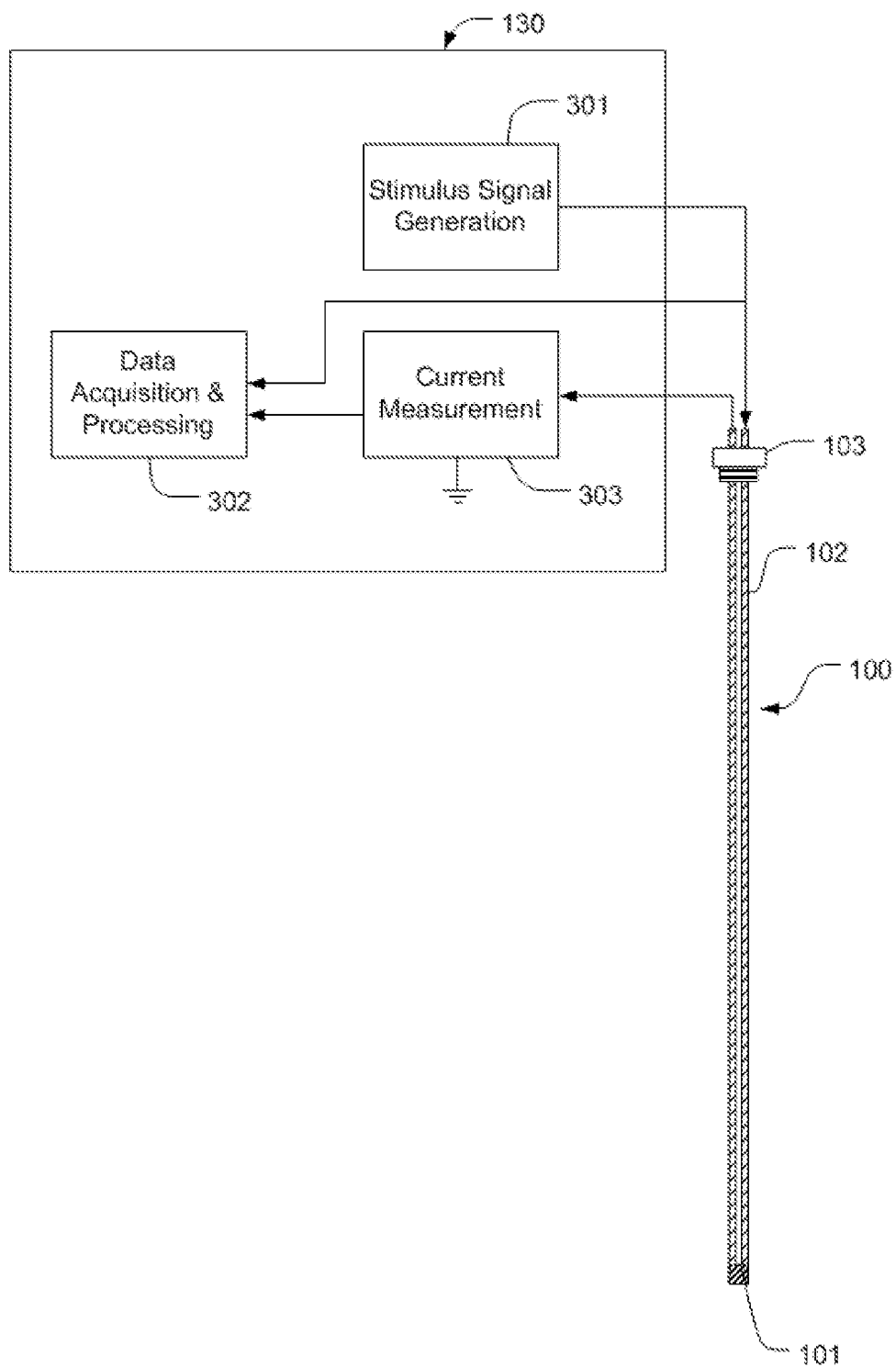
FIG. 3 shows an exemplary circuit for obtaining sensing values from a capacitive sensor.

In the step 201, a variety of methods, such as measuring applied voltage and induced current, and measuring charging time after a constant voltage is applied, can be used in measuring the impedance values Z of the capacitive sensor 100. Among these methods, to avoid the polarization of the electrodes, the method of applying a low alternate voltage and measuring induced current is preferred. An apparatus of using this method is shown in FIG. 3. In this apparatus, an alternate voltage signal is generated from a stimulus signal generation block 301 in the controller 130, and applied to one of the electrodes in the capacitive sensor 100. The amplitude of the alternate voltage signal should be low enough not causing significant redox reactions on the electrode, and the current induced by the alternate voltage signals is converted to a voltage signal in a current measurement block 303 in the controller 130, which is also connected to the other electrode of the capacitive sensor 100. The voltage signal generated in the current measurement block 303 is then sent to a data acquisition and processing block 302 together with the applied voltage signal generated in the stimulus signal generation block 301, and the signals are further processed therein. Impedance is then calculated with the processed signals.

In the step 202, slosh can be detected by monitoring the changing rate of the impedance values Z, e.g., if the changing rate is higher than a threshold, then a slosh is detected. In addition to the impedance changing rate, some other indications, such as the movement status of the fluid, can also be used in slosh detection. For example, when the fluid level and quality sensing device is disposed in a fluid tank of a vehicle, the vehicle speed can be used as an indication of slosh. One exemplary algorithm using the vehicle speed could be: if the vehicle stops, i.e., the vehicle speed is zero, then there is no slosh a short time after the moment when the vehicle speed becomes zero, and when vehicle speed is higher than zero, then a slosh is detected. These indications can also be used for diagnosing anomalies in the capacitive sensor 100 and the vehicle speed sensors. In the above example, if the changing rate of the impedance value Z is still higher than a threshold a short time after the moment when the vehicle speed becomes zero, then there is an error in either the capacitive sensor reading or the sensing values obtained from the vehicle speed sensors, and a fault flag Fs is set. When a slosh is certainly detected, e.g., a short time after the moment when the vehicle speed changes to zero or from zero to another value, if the changing rate of impedance value Z is lower than another threshold, then an issue exists in either the capacitive sensor or the vehicle speed sensors, and a fault flag Fk is set.

In addition to detecting issues in the sensors and the fluid, the quick response and continuous reading of the capacitive sensor 100 also allow it to be used in improving fluid level sensing performance. Referring back to FIG. 1b, when a reed switch fluid level sensor is used, the level sensing values are discrete, i.e. limited to the positions of the switches 117, only a few step values can be generated by the sensor. The resolution of the reed switch fluid level sensor is limited by the sensitivity of the magnetic switches 117 and the magnetic force created by the float 114. If two adjacent switches are too close to each other, then they may be closed simultaneously, causing reading issues.

The discrete sensing may limit the applications of the reed switch fluid level sensors. For example, in applications where the change of fluid level needs to be detected, the discrete sensing limits the resolution of the detection, since the fluid level change in between two discrete values cannot be detected. With the capacitive sensor 100, the sensing resolution can be greatly increased. One exemplary method for the resolution improvement is using impedance of the capacitive sensor 100 to calculate fluid level reading in between two discrete steps of the reed switch sensor 110, i.e., upon a step change of discrete sensing values of the reed switch sensor 110, the relative change in the impedance of the capacitive sensor 100 is used to calculate the corresponding fluid level change, which is then added to the discrete sensing value of the reed switch sensor 110 to calculate the fluid sensing value. To increase the calculation accuracy, the sensing value obtained from the temperature sensor 120 can be further used for compensating the calculation, e.g. a lookup table with two inputs of the temperature sensing value and the impedance change value can be used in calculating the relative fluid level change.

When a non-contact fluid level sensor, such as the sensor 110 of FIG. 1c is used, sometimes changes in fluid surface shape may cause an error signal. Though normally this error signal can be detected by the sensor and filtered out, sensing values are not available when this error appears. The impedance of the capacitive sensor 100 can be used to provide sensing values when such a sensing error in the fluid level sensor is detected. In an exemplary method, when an error is detected in the non-contact fluid level sensor 110, the relative level change from the last valid sensing value is calculated by using the change in the impedance of the capacitive sensor 100 and the temperature sensing values provided by the sensor 120 if more accurate calculation is required. The fluid level sensing value is then obtained by adding the last valid sensing value to the calculated relative level change value.

Figure 4:
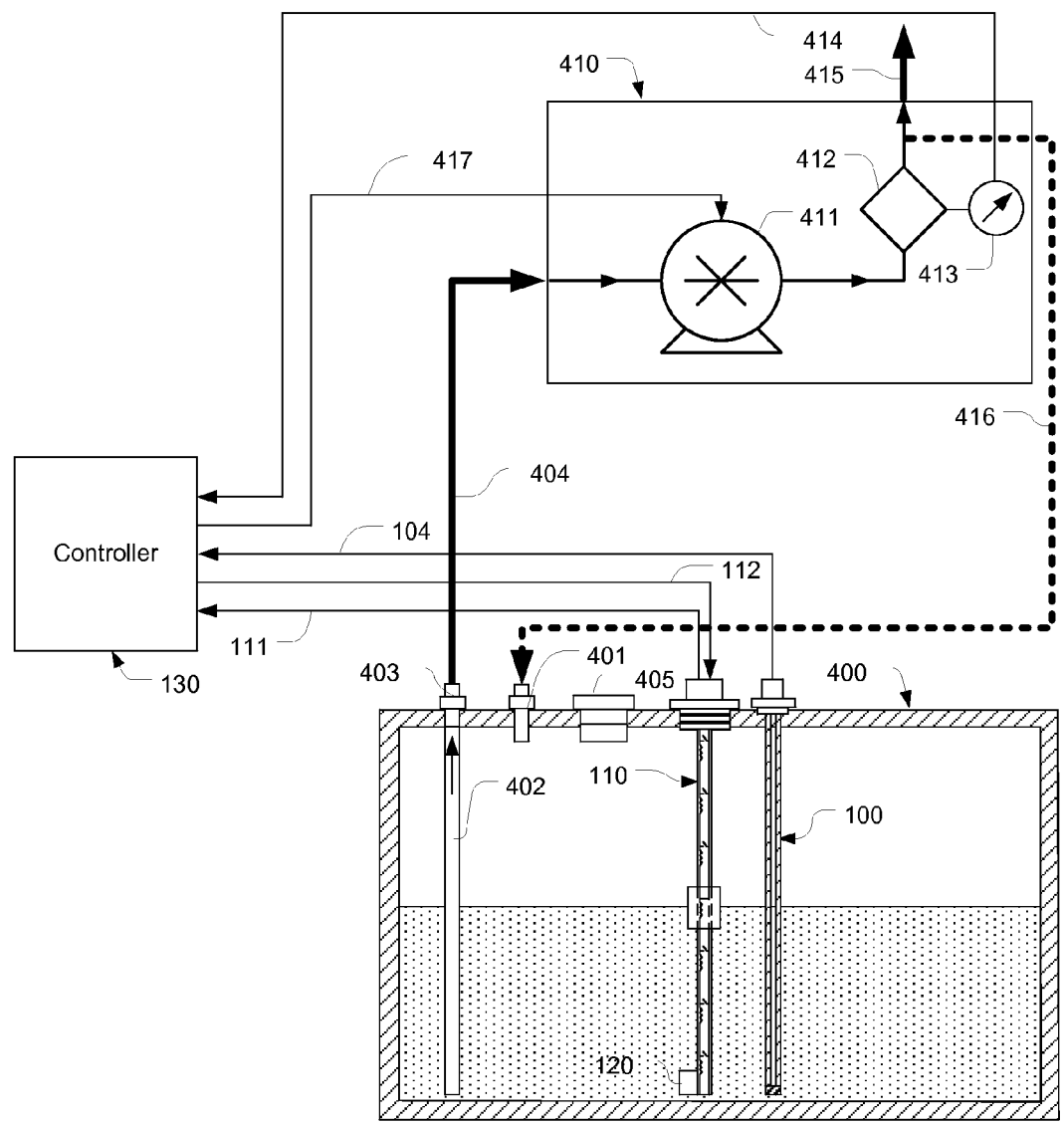
FIG. 4 is diagrammatic illustration of a DEF dosing apparatus with a fluid level and quality sensing device.

The fluid level and quality sensing device of FIG. 1a can also be used in examining issues in a fluid delivery system. An example of such a fluid delivery system is a DEF delivery system of a SCR apparatus for reducing NOx in exhaust gas of a diesel engine. Referring to FIG. 4, a DEF delivery system includes a DEF supply module 410, a DEF tank 400 in which the fluid level sensor 110, the temperature sensor 120, and the capacitive sensor 100 are positioned, and the controller 130. The DEF tank 400 has a cap 405 through which DEF is refilled, and the DEF supply module 410 further includes a pump 411 controlled by the controller 130 through signal lines 417, a pressure control vessel 412 with a pressure sensor 413, which provides sensing signals to the controller 130 through signal lines 414. Under the control of the controller 130, the pump 411 draws DEF from the DEF tank 400 though a tubing 402 fluidly connected to a port 403, and then through a passage 404 delivers it into the pressure control vessel 412, the pressure inside which is then used by the controller 130 to adjust the pumping rate for controlling the pressure within a predetermined range. Under the pressure in the vessel 412, DEF is released through a passage 415, which is fluidly connected to an injector (not shown in FIG. 4), and the releasing rate, i.e., the dosing rate, can be controlled by opening the injector for an adjustable period of time in a repeating cycle according to a dosing command. The dosing accuracy of the delivery system is affected by the pressure control performance. To more accurately control the DEF pressure, sometimes DEF in the pressure control vessel 412 needs to be released back to the DEF tank 400 through a passage 416 and a port 401 on the DEF tank.

A variety of methods can be used for diagnosing the DEF delivery system of FIG. 4. One exemplary method is comparing the DEF volume change in the tank 400, which can be calculated with sensing values obtained from the capacitive sensor 100, to the dosing amount calculated by integrating the dosing rate commands. If the DEF volume change doesn't match the dosing amount, then there is an issue in the delivery system, e.g., the injector is stuck closed, or an in-range high error exists in the pressure sensor 413, and fault flags are set.

Figure 5A:
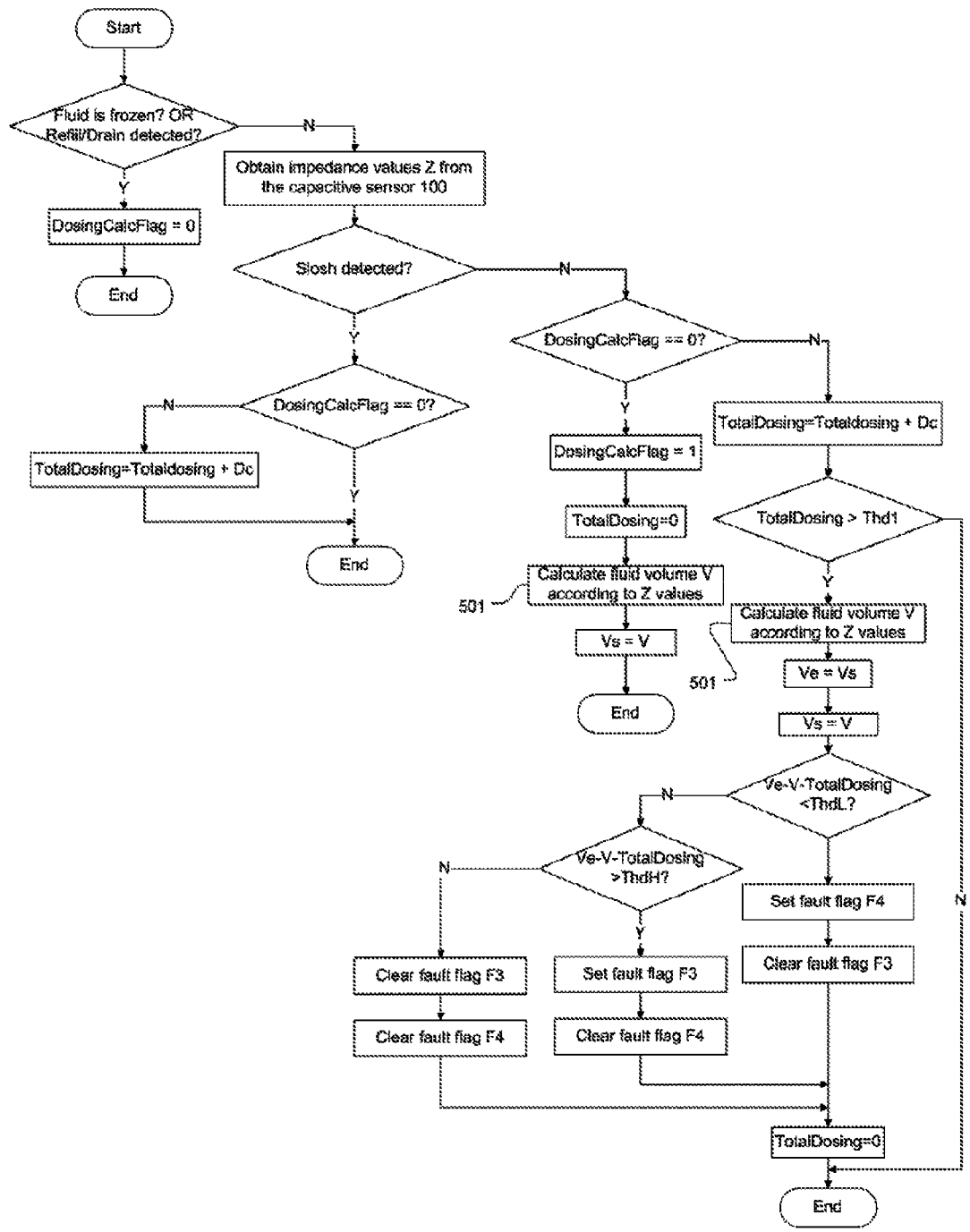
FIG. 5a is a flowchart of an exemplary service routine for a timer based interrupt running periodically for detecting issues in a DEF dosing apparatus with DEF volume calculated using sensing values obtained from a capacitive sensor.

The exemplary diagnosis method can be realized with a service routine running periodically for a timer based interrupt. Referring to FIG. 5a, in such a routine, the fluid status is examined first. If the fluid is frozen or a refill/drain event is detected then the routine ends after a flag DosingClacFlag is reset to 0, otherwise, the impedance values Z is obtained from the capacitive sensor 100. If a slosh is detected thereafter, then the value of the flag DosingClacFlag is checked. If it is 0, then the routine ends, otherwise, a variable TotalDosing is incremented by the dosing amount in an execution cycle of the service routine, Dc. When no slosh is detected and the value of the flag DosingCalcFlag is 0, then the flag value is set to 1, and the variable TotalDosing is set to 0. The routine ends after the fluid volume V is calculated according to the impedance values Z in a step 501, and the V value is assigned to a variable Vs. When no slosh is detected and the value of the flag DosingCalcFlag is not zero, then the variable TotalDosing is incremented by the Dc value and the TotalDosing value is compared to a threshold Thd1. If it is higher than the threshold Thd1, then the routine ends, otherwise, the fluid volume V is calculated in the step 501, and the V value is assigned to the variable Vs after the Vs value is assigned to a variable Ve. The difference between the Ve value and the V value, Ve−V, is the DEF volume change in dosing. Compared to the value of the variable TotalDosing, if the difference value Ve−V is overly low, i.e., the value of Ve−V−TotalDosing is lower than a threshold ThdL, then a fault flag F4 is set and a fault flag F3 is cleared. If the difference value is overly high, i.e., the value of Ve−V−TotalDosing is higher than a threshold ThdH, then the fault flag F3 is set and the fault flag F4 is set. Both of the fault flags F3 and F4 are cleared if the value of Ve−V−TotalDosing is in between thresholds ThdL and THdH. The variable TotalDosing is reset to zero thereafter, and the routine ends.

In the service routine of FIG. 5a, the refill/drain can be detected either with a cap sensor that monitors the cap status (e.g. the status of the cap 405 in FIG. 4), or by using the change in the impedance value Z when vehicle speed and engine speed is zero. Normally refill or drain is only allowed when a vehicle stops and its engine is keyed off due to safety concerns, and no DEF is dosed when engine speed is zero.

In the fluid delivery system of FIG. 4, the fluid volume V is a function of the fluid level L, while the impedance value Z is determined by the fluid level L. Thereby, in the step 501, the fluid volume V can be calculated using the impedance values Z, according to the following equation, and the sensing value T obtained from the temperature sensor 120 can be used for further compensation:

$$V=f(Z,T) \quad (1)$$

The function in equation (1) can be realized with a lookup table populated using results obtained from a matrix test, in which impedance of the capacitive sensor 110 is measured under different temperatures and fluid levels.

Figure 5B:
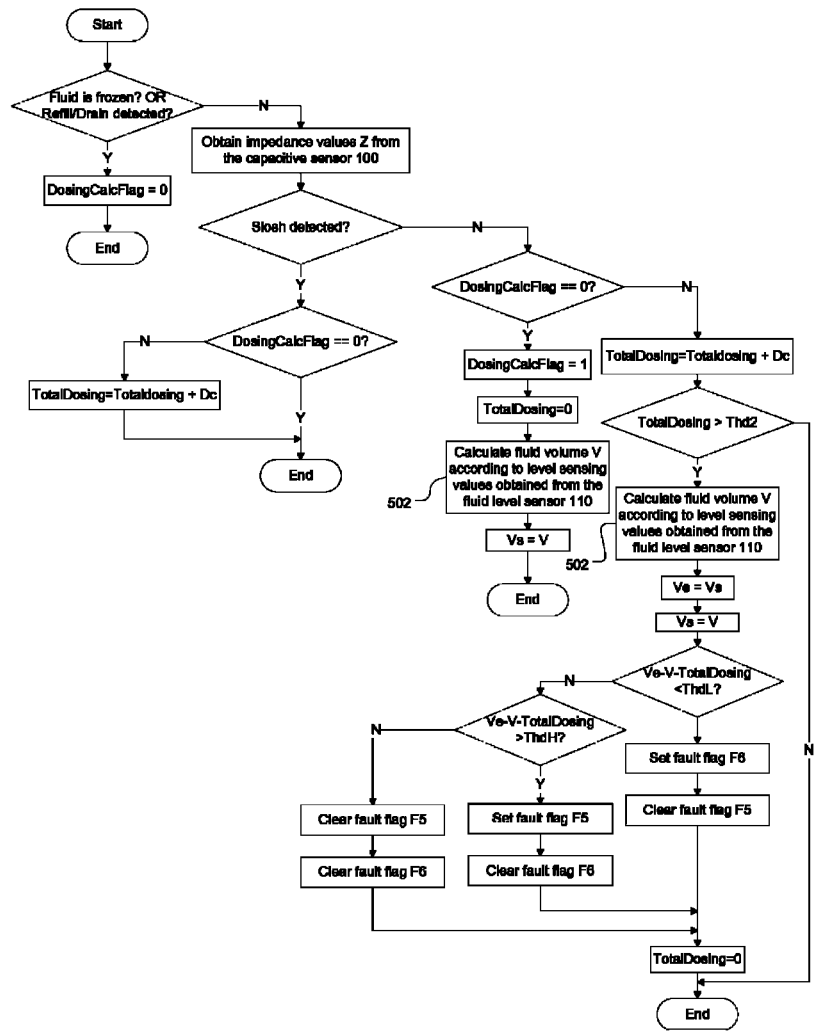
FIG. 5b is a flowchart of an exemplary service routine for a timer based interrupt running periodically for detecting issues in a DEF dosing apparatus with DEF volume calculated using sensing values obtained from a fluid level sensor.

In addition to using the impedance value Z in calculating the DEF volume V, the sensing value obtained from the fluid level sensor 110, R, can also be used for this purpose. Referring to FIG. 5b, when the sensing value R is used in the calculation, a similar service routine as that of FIG. 5a can be used in determining values for fault flags F5 and F6. In this service routine, the volume V is calculated in a step 502, and if the R value is not sensitive to fluid temperature (e.g. when a reed switch sensor as shown in FIG. 1b is used), the following function can be used in the calculation:

$$V=g(R) \quad (2)$$

As that in equation (1), the function in equation (2) can also be calculated using a lookup, and the elements in the lookup table can be populated with results obtained from a test in which the R value is measured with different fluid levels.

In the system of FIG. 4, errors in fluid quality and the fluid level and quality sensing devices together with issues in the fluid delivery system and vehicle speed sensors can be detected with the fault flags F1-F6, Fs and Fk. A matrix of the relations between the fault flags and the errors and issues is shown in FIG. 6. In the matrix, all the "in-range" errors are rationality errors that make sensing values look reasonable, however, inaccurate. With "in-range" errors, though a sensing value is still in the valid sensing range of a sensor, it is out of the error tolerance of the sensor. In FIG. 6, the "in-range" errors include an "in-range high" error, which causes a sensing value obtained from a sensor greater than its error tolerance, an "in-range low" error, with which a sensing value is lower than its error tolerance, and a "stuck-in-range" error, which causes a sensor lose its sensitivity and the sensing value "stays" at constant value or in a narrow band in the sensing range.

In the relations between the errors and issues of FIG. 6, "X" denotes an error can be triggered by a fault flag. For example, when the fault flag F1 is set, then there are five possible errors in the fluid delivery system, including a fluid quality error, an in-range high error and a stuck-in-range error of the sensor 110, and an in-range low error and a stuck-in-range error of the sensor 100. As shown in FIG. 6, the fault flags F1 and F2, F3 and F4, and F5 and F6, are pairs. In the fault pairs, the fault flags are mutual-exclusive, i.e., the flags F1 and F2, F3 and F4, or F5 and F6 cannot be set at the same time. However, the fault flags pairs can work together to further isolate errors. For example, if a fault flag F1 and F3 are set at the same time, then according to the matrix of FIG. 6, the error must be the stuck-in-range error of the sensor 100 if the fault flag is caused by a single error, since only this error can set both of the F1 and the F3 fault flags.

When the DEF delivery system of FIG. 4 is used in a SCR apparatus of a diesel engine system, the DEF volume change can be further used in diagnosing the integrity of the system.

In the diesel engine system, the SCR apparatus is used for reducing NOx in exhaust air, and DEF is dosed into exhaust air through the DEF delivery system. The dosed DEF is converted into ammonia through thermolysis and hydrolysis, and the ammonia reacts with the NOx in exhaust air in the SCR catalyst. The consumption ratio between the DEF to the NOx concentration in exhaust air, which is further affected by the energy released in burning fuel, is a value in a range with an upper limit restricted by the maximum allowed ammonia slip that flows out into ambient and a lower limit determined by the maximum allowed system NOx emission level. If the DEF consumption ratio is lower than the lower limit or higher than the upper limit, then an issue exists in the diesel engine system. Such an issue could be either a component failure, e.g. fuel injectors being stuck closed or stuck open, or a tampering, e.g., bypassing engine exhaust air flow from the SCR apparatus.

Figure 7:
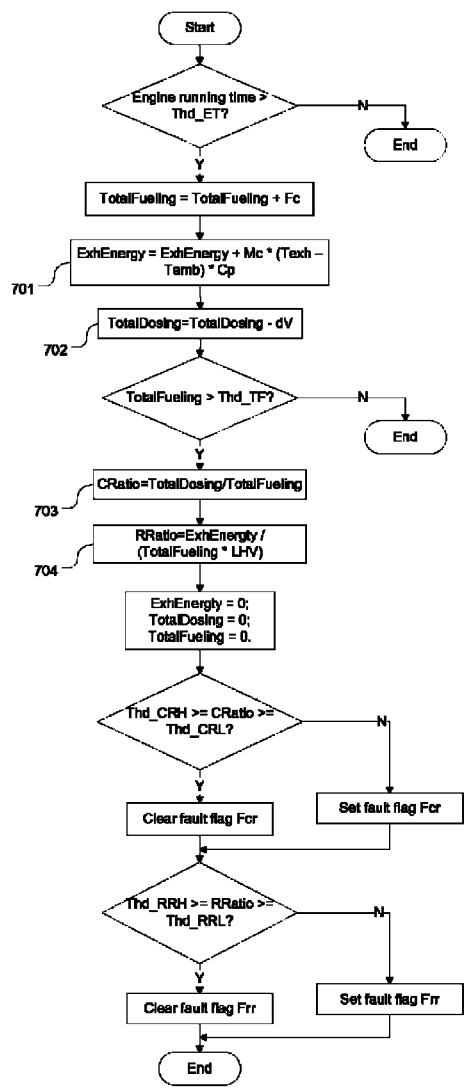
FIG. 7 is a flowchart of an exemplary service routine for a timer based interrupt running periodically for detecting issues in an engine system with a DEF dosing apparatus.

An exemplary method for detecting system integrity includes calculating a consumption ratio of DEF dosing amount to engine fueling amount, and an energy ratio of an enthalpy change in exhaust air to the total energy released by burning fuel. The energy ratio can be used for further isolating problems in the engine and in the SCR apparatus. An algorithm of the exemplary method can be realized using a service routine running periodically for a timer based interrupt. Referring to FIG. 7, in such a routine, the engine running time is examined first. If the engine running time is equal to or shorter than a threshold Thd_ET, i.e., when the engine is still cold, then the routine ends, otherwise, a variable TotalFueling is incremented by the fueling amount in an execution cycle of the service routine, Fc. A variable ExhEnergy is calculated thereafter in a step 701 and in a next step 702, another variable TotalDosing is accumulated by the DEF volume change an execution cycle, −dV. In the next step, the value of the variable TotalFueling is compared to a threshold Thd_TF. If the TotalFueing value is not higher than Thd_TF, the routine ends, otherwise, in a step 703, a consumption ratio value is calculated by dividing the TotalDosing value by the TotalFueling value, and is assigned to a variable CRatio. In a following step 704, an energy ratio value is calculated and assigned to a variable RRatio. After the calculation, the variables ExhEnergy, TotalDosing, and TotalFueling are reset to zero, and the CRation value is compared to a consumption ratio range with an upper boundary of Thd_CRH and a lower boundary of Thd_CRL. If it is out of the boundary, then a fault flag Fcr is set, otherwise, the fault flag Fcr is cleared. The RRatio value is also compared to an energy ratio range with an upper boundary of Thd_RRH and a lower boundary of Thd_RRL. Before the routine ends, a fault flag Frr is set when the RRatio value is out of the energy ratio range, and is cleared if the RRatio value is within the range.

In the service routine of FIG. 7, the calculation in the step 701 is to calculate the enthalpy change of exhaust air when its temperature rises from ambient temperature to the current temperature. In the equation of the step 701 shown in FIG. 7, Mf is the mass flow of the exhaust air in an execution cycle of the service routine, Texh the exhaust air temperature, Tamb the ambient temperature, and Cp the average heat capacity at constant pressure. In the step 702, the DEF volume change dV is calculated using the difference between the DEF volume values calculated in the current cycle and the previous cycle. And the DEF volume values can be calculated using level sensing values obtained from the fluid level sensor 110. In calculating the energy ratio value, the equation in the step 704 includes a calculation of combustion energy released in burning fuel. In this calculation, LHV is the low heating value of the fuel injected in the engine, and the combustion energy is calculated using the product of the TotalFueling value and LHV.

The values of the fault flags Frr and Fcr provide more information about the system. Together with other fault flags, errors in the system can be further isolated. For example, when a fault flag Fcr is set, there could be an engine error, an error in the SCR apparatus, or a system integrity error, if a single error causes this problem. If there is the fault flag Frr is set as well, then the error is an integrity error, and low exhaust air enthalpy causes low DEF dosing, while if there are SCR apparatus fault flags being set, e.g., an F5 flag is set, then the problem is a dosing issue, which causes low dosing rate.

Although the apparatus and method of the invention are described herein in relation to the preferred embodiments shown in FIGS. 1-7, certain design alternations and modifications will become apparent to those of ordinary skill in the art upon reading this disclosure in connection with the accompanying drawings. It is intended, however, that the scope of the invention be limited only by the appended claims.

What is claimed:

1. A fluid level and quality sensing device, comprising:
   a fluid level sensing means for measuring a level of a fluid proving a level sensing signal indicative of said level of said fluid;
   a capacitive sensor including at least two electrodes positioned in said fluid providing an impedance sensing signal at least indicative of said level of said fluid;
   a controller configured to
      determine an expected impedance range including an upper boundary value and a lower boundary value in response to at least said level sensing signal, and
      generate a fault signal in response to at least said expected impedance range and said impedance sensing signal.

2. The fluid level and quality sensing device of claim 1, wherein said fault signal corresponds to a fault of said fluid.

3. The fluid level and quality sensing device of claim 1, further comprising:
   a temperature sensor providing a temperature sensing signal indicative of a temperature of said fluid.

4. The fluid level and quality sensing device of claim 3, wherein said controller is further configured to determine said expected impedance range in response to said temperature sensing signal.

5. The fluid level and quality sensing device of claim 3, wherein said controller is further configured to generate said fault signal in response to said temperature sensing signal.

6. The fluid level and quality sensing device of claim 1, wherein said controller is further configured to generate a slosh sensing signal indicative of a slosh of said fluid in response to at least a changing rate of sensing values obtained from said impedance sensing signal.

7. The fluid level and quality sensing device of claim 6, wherein said controller is further configured to generate said fault flag in response to said slosh sensing signal.

8. The fluid level and quality sensing device of claim 1, wherein said controller is further configured to generate a level sensing value in response to at least said level sensing signal and said impedance sensing signal.

9. The fluid level and quality sensing device of claim 8, further comprising a temperature sensor providing a temperature sensing signal indicative of a temperature of said fluid, wherein said controller is further configured to generate a level sensing value in response to at least said level sensing signal, said impedance sensing signal, and said temperature sensing signal.

10. A fluid delivery diagnostic system, comprising:
   a fluid tank containing a fluid;
   a fluid level sensing means for measuring a level of said fluid in said fluid tank proving a level sensing signal indicative of said level of said fluid;
   a capacitive sensor including at least two electrodes positioned in said fluid providing an impedance sensing signal at least indicative of said level of said fluid;
   an injector;
   a pump for drawing said fluid from said fluid tank and providing said reductant fluid to said injector;
   an injection controller configured to control a releasing rate of said fluid in response to a pre-determined injection-rate command value by energizing said injector open for a period of time in a repeating cycle; and
   a diagnostic controller configured to
      obtain an injection rate value indicative of said releasing rate of said fluid from said injection controller, and
      generate a system fault signal in response to said level sensing signal, said impedance sensing signal, and said injection rate value.

11. The fluid delivery diagnostic system of claim 10, wherein said diagnostic controller is further configured to determine an expected impedance range including an upper boundary value and a lower boundary value according to at least said level sensing signal, and generate a component fault signal in response to at least said expected impedance range and said impedance sensing signal.

12. The fluid delivery diagnostic system of claim 11, wherein said diagnostic controller is further configured to generate said system fault signal in response to said component fault signal.

13. The fluid delivery diagnostic system of claim 10, wherein said diagnostic controller is further configured to generate a slosh sensing signal indicative of a slosh of said fluid in response to at least a changing rate of said impedance sensing signal.

14. The fluid delivery diagnostic system of claim 13, wherein said diagnostic controller is further configured to
   determine a first fluid level at a first moment in response to said slosh sensing signal,
   determine a second fluid level at a second moment in response to said slosh sensing signal,
   determine a volume change of said fluid according to said first fluid level and said second fluid level,
   determine a released fluid amount according to said injection rate value, and
   generate said system fault signal in response to said volume change and said released fluid amount.

15. The fluid delivery diagnostic system of claim 14, further comprising a temperature sensor providing a temperature sensing signal indicative of a temperature of said fluid, wherein said diagnostic controller is further configured to determine said first fluid level and said second fluid level in response to said impedance sensing signal and said temperature sensing signal.

16. The fluid delivery diagnostic system of claim 14, wherein said diagnostic controller is further configured to determine said first fluid level and said second fluid level in response to said level sensing signal.

17. A diagnostic system for monitoring an engine system with an exhaust gas treatment apparatus, comprising:
   an engine;
   an engine control module that controls a fueling rate of said engine;
   an exhaust gas temperature sensor for measuring a temperature of exhaust gas generated from said engine;
   an exhaust flow-rate sensor for measuring a flow rate of exhaust gas generated from said engine;
   a fluid tank containing a reductant fluid;
   a dosing system including
      an injector,
      a pump for drawing said reductant fluid from said fluid tank and providing said reductant fluid to said injector, and
      an injection controller configured to control a releasing rate of said reductant fluid in response to a pre-determined dosing-rate command value by energizing said injector open for a period of time in a repeating cycle; and
   a diagnostic controller configured to
      obtain a fueling rate value indicative to said fueling rate of said engine from said engine control module,
      obtain an exhaust temperature sensing value indicative of said temperature of exhaust gas from signals generated by said exhaust gas temperature sensor,
      obtain an exhaust flow-rate sensing value indicative of said flow rate of exhaust gas from signals generated by said exhaust flow-rate sensor,
      determine a combustion energy value according to said fueling rate value, an exhaust air enthalpy value according to said exhaust temperature sensing value and said exhaust flow-rate sensing value, and an energy ratio value according to said combustion energy value and said exhaust air enthalpy value, and
      generate an engine system fault signal in response to said energy ratio value.

18. The diagnostic system of claim 17, further comprising:
   a fluid level sensing means for measuring a level of said reductant fluid in said fluid tank providing a level sensing signal indicative of said level of said reductant fluid; and
   a capacitive sensor including at least two electrodes positioned in said fluid providing an impedance sensing signal at least indicative of said level of said reductant fluid;
   wherein said diagnostic controller is further configured to
      determine a reductant volume value in response to said level sensing signal and said impedance sensing signal, and a reductant consumption ratio value in response to said reductant volume value and said fueling rate value, and
      generate a dosing system fault signal in response to said reductant consumption ratio value.

19. The diagnostic system of claim 18, wherein said diagnostic controller is further configured to
   determine an expected impedance range including an upper boundary value and a lower boundary value according to at least said level sensing signal, and
   generate a component fault signal in response to at least said expected impedance range and said impedance sensing signal.

20. The diagnostic system of claim 19, wherein said diagnostic controller is further configured to determine whether an error exists in said fluid level sensing means, said capacitive sensor, and said reductant fluid in said fluid tank in response to said component fault signal, determine whether an error exists in said engine system in response to said engine system fault signal, and determine whether an error exists in said dosing system in response to said dosing system fault signal after said diagnostic controller determines no error exists in said engine system, said fluid level sensing means, said capacitive sensor, and said reductant fluid in said fluid tank.

* * * * *